(12) United States Patent
Hirano et al.

(10) Patent No.: US 7,894,051 B2
(45) Date of Patent: Feb. 22, 2011

(54) RETICLE DEFECT INSPECTION APPARATUS AND RETICLE DEFECT INSPECTION METHOD

(75) Inventors: Ryoichi Hirano, Tokyo (JP); Riki Ogawa, Kanagawa (JP)

(73) Assignees: Kabushiki Kaisha Toshiba, Tokyo (JP); NEC Corporation, Tokyo (JP)

( * ) Notice: Subject to any disclaimer, the term of this patent is extended or adjusted under 35 U.S.C. 154(b) by 261 days.

(21) Appl. No.: 12/061,118

(22) Filed: Apr. 2, 2008

(65) Prior Publication Data
US 2008/0259323 A1 Oct. 23, 2008

(30) Foreign Application Priority Data
Apr. 18, 2007 (JP) ............................. 2007-109289

(51) Int. Cl.
*G01N 21/00* (2006.01)
(52) U.S. Cl. ................................. 356/237.2; 356/237.3
(58) Field of Classification Search .... 356/237.1–237.5
See application file for complete search history.

(56) References Cited

U.S. PATENT DOCUMENTS 7,251,033 B1* 7/2007 Phan et al. ................. 356/432
2004/0117055 A1* 6/2004 Seidel et al. ................. 700/121
2007/0030471 A1* 2/2007 Troost et al. .................. 355/67

FOREIGN PATENT DOCUMENTS

| JP | 11-83753 | 3/1999 |
|----|----------|--------|
| JP | 2002-75815 | 3/2002 |
| JP | 2006-98156 | 4/2006 |

* cited by examiner

*Primary Examiner*—Michael P Stafira
(74) *Attorney, Agent, or Firm*—Oblon, Spivak, McClelland, Maier & Neustadt, L.L.P.

(57) ABSTRACT

A reticle defect inspection apparatus that controls damage of a reticle by irradiation with an inspection light when the reticle is caused to be at rest is provided. The reticle defect inspection apparatus is a reticle defect inspection apparatus for inspecting for defects on a reticle using a pattern image obtained by irradiating the reticle on which a pattern is formed with light. The reticle defect inspection apparatus has a dose monitoring part for measuring a dose of the light to the reticle, a comparing part for comparing, after calculating accumulated irradiation from the dose measured by the dose monitoring part, the accumulated irradiation with a preset threshold, and a stop mechanism for stopping irradiation of the reticle with the light when, as a result of the comparison, the accumulated irradiation exceeds the threshold.

10 Claims, 4 Drawing Sheets

SCAN WIDTH

RETICLE DEFECT INSPECTION APPARATUS AND RETICLE DEFECT INSPECTION METHOD

CROSS-REFERENCE TO RELATED APPLICATION

This application is based upon and claims the benefit of priority from Japanese Patent Application No. 2007-109289, filed on Apr. 18, 2007, the entire contents of which are incorporated herein by reference.

FIELD OF THE INVENTION

The present invention relates to a reticle defect inspection apparatus and a reticle defect inspection method for performing an inspection using an image obtained by irradiating a sample with light.

BACKGROUND OF THE INVENTION

Some patterns constituting a large-scale integrated circuit (LSI), as exemplified by DRAM of a gigabit class, have a minimum design rule reduced from submicron up to the order of nanometer. One of major causes for reduced yields in a manufacturing process of such an LSI includes defects contained in a reticle (also called a mask) used when a hyperfine pattern is exposed and transcribed onto a semiconductor wafer using lithography technology.

With increasingly finer pattern dimensions of LSI formed on a semiconductor wafer, dimensions in which such pattern defects must be detected are also becoming extremely smaller. Thus, reticle defect inspection apparatuses for inspecting for extremely small defects are vigorously being developed (for example, JP-A 2006-98156 (KOKAI)).

One method of improving performance of an exposure device to a semiconductor wafer is to make wavelengths of a light source shorter. Thus, DUV (Deep Ultra Violet) light having short wavelengths, for example, a light of the wavelength 193 nm using an ArF laser is used as the light source of an exposure device. In addition, to further enhance resolution, using EUV (Extreme Ultra Violet) light, for example, a light of the wavelength of about 13.5 nm using plasma emission is also being examined.

SUMMARY OF THE INVENTION

A reticle defect inspection apparatus according to an embodiment of the present invention is a reticle defect inspection apparatus for inspecting for defects on a reticle using a pattern image obtained by irradiating the reticle on which a pattern is formed with light. The reticle defect inspection apparatus includes a dose monitoring part for measuring a dose of the light to the reticle, a comparing part for comparing, after calculating accumulated irradiation from the dose measured by the dose monitoring part, the accumulated irradiation with a preset threshold, and a stop mechanism for stopping irradiation of the reticle with the light when, as a result of the comparison, the accumulated irradiation exceeds the threshold.

A reticle defect inspection method according to an embodiment of the present invention is a reticle defect inspection method for inspecting for defects on a reticle using a pattern image obtained by irradiating the reticle on which a pattern is formed with light. The reticle defect inspection method includes inspecting the pattern image by irradiating the reticle with the light while the reticle is at rest, and stopping irradiation of the reticle with the light when accumulated irradiation of the reticle with the light exceeds a preset threshold.

DETAILED DESCRIPTION OF THE EMBODIMENTS

Figure 1:
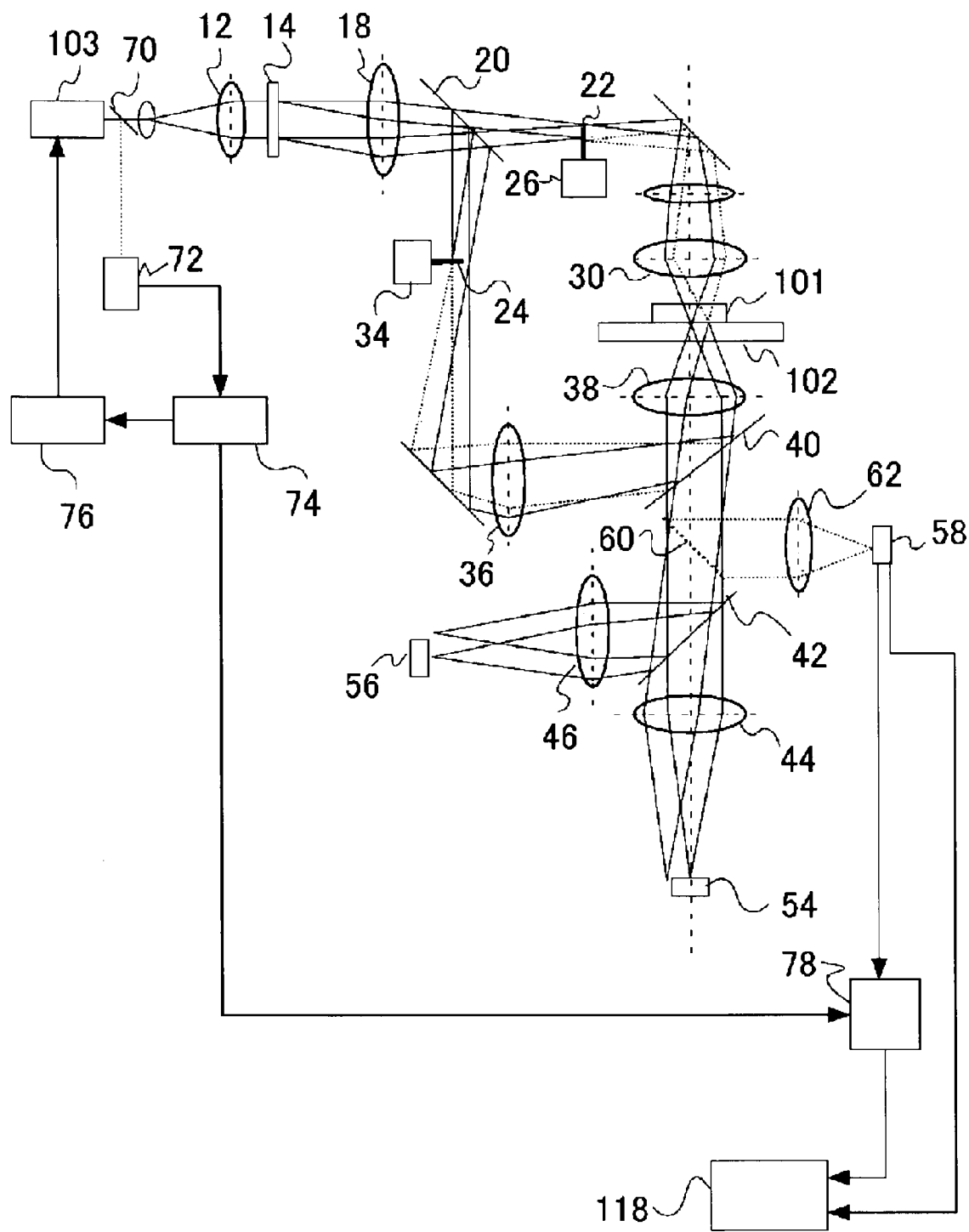
FIG. 1 is a diagram showing principal parts of an optical system and a control system of a reticle defect inspection apparatus in a first embodiment.

Embodiments of the present invention will be described below with reference to drawings.

When a reticle inspection is performed, pattern images are usually captured while a reticle, which is a sample to be inspected, is moved to enhance inspection efficiency. In contrast, if a defect is detected by the inspection in which the reticle is moved, an inspection may be performed this time by capturing pattern images while the reticle is caused to be at rest (hereinafter, an inspection while a reticle is at rest may also be called observation) to confirm the defect.

In an inspection in which a reticle is caused to be at rest, as described above, accumulated irradiation (or an amount of energy) of the reticle with an inspection light dramatically increases compared with an inspection in which a reticle is moved. More specifically, if a laser light of 199 nm is used, for example, energy of about 3.5 mJ/cm$^2$ is shone on a reticle surface when an inspection is performed by moving a reticle using sensor resolution of 70 nm. In defect observation in which a reticle is caused to be at rest, on the other hand, energy in accordance with an observation time is accumulated on the reticle surface because the inspection light is continuously shone on an observation location of the reticle. If the reticle surface illumination during observation is 0.7 W/cm$^2$, for example, one second of observation accumulates energy 0.7 W/cm$^2 \times 1$ (sec)=0.7 J/cm$^2$ and 10 seconds of observation 0.7 W/cm$^2 \times 10$ (sec)=7 J/cm$^2$. Therefore, 1000 times or more energy will be shone for 10 seconds of observation compared with an inspection. Thus, a reticle will be damaged, that is, the transmittance and reflectance will change during observation while the reticle is at rest. Such damage is a problem because the damage could be a factor causing a pattern transcription failure when performing exposures using the reticle.

In the case of exposure device using EUV light, the transmittance of EUV light with respect to substance is extremely low and therefore, for example, a reflection type reticle in which a pattern is formed by an optical absorber on a multilayer film made of molybdenum (Mo) and silicon (Si) is required. Since, compared with a transmission type reticle, such a reflection type reticle has no way out for an inspection light, energy due to irradiation with the inspection light tends to accumulate in a pattern portion. Therefore, it is conceivable that a problem of reticle damage during inspection or observation will be serious.

Embodiments of the present invention provide a reticle defect inspection apparatus and a reticle defect inspection method that control damage of a reticle caused by irradiation with an inspection light when the reticle is inspected while the reticle is caused to be at rest.

First Embodiment

A reticle defect inspection apparatus according to the present embodiment is a reticle defect inspection apparatus for inspecting for defects on a reticle using a pattern image obtained by irradiating the reticle on which a pattern is formed with light. The reticle defect inspection apparatus includes a dose monitoring part for measuring a dose of the light to the reticle, a comparing part for comparing, after calculating accumulated irradiation from the dose measured by the dose monitoring part, the accumulated irradiation with a preset threshold, and a stop mechanism for stopping irradiation of the reticle with the light when, as a result of the comparison, the accumulated irradiation exceeds the threshold.

In the present embodiment, a reticle, which is a sample to be inspected by the reticle defect inspection apparatus, is a transmission type reticle for DUV exposure. An inspection apparatus that can perform a simultaneous inspection of transmission and reflection of the transmission reticle using both a transmitted light and a reflected light as inspection lights is taken as an example for a description that follows.

Figure 2:
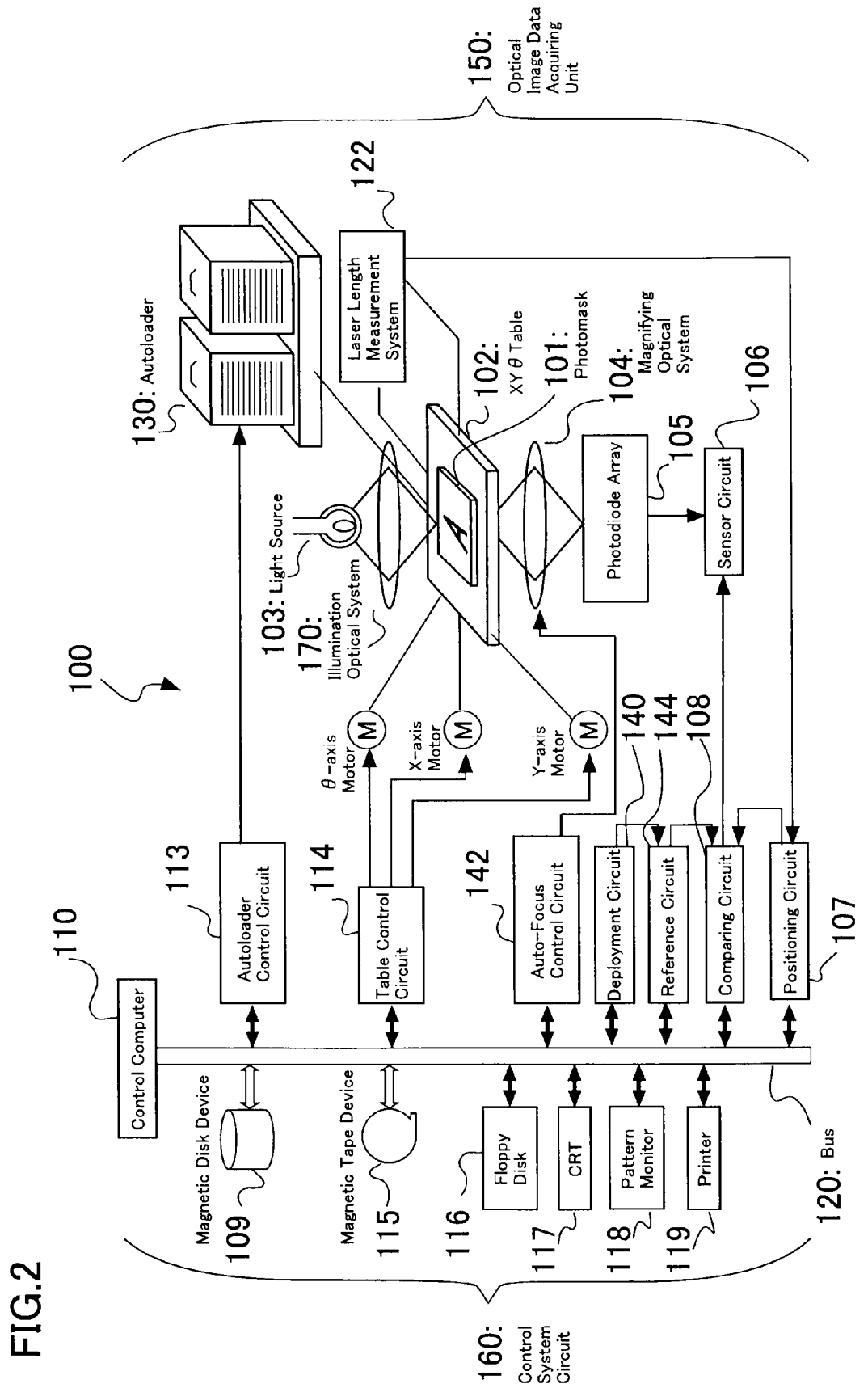
FIG. 2 is a diagram of an overall configuration and functions of the reticle defect inspection apparatus in the first embodiment.

FIG. 2 is a diagram illustrating an overall configuration and a functional overview of the reticle defect inspection apparatus in the present embodiment. A reticle defect inspection apparatus 100 shown in FIG. 2 includes an optical image data acquisition part 150 and a control system circuit 160.

Figure 3:
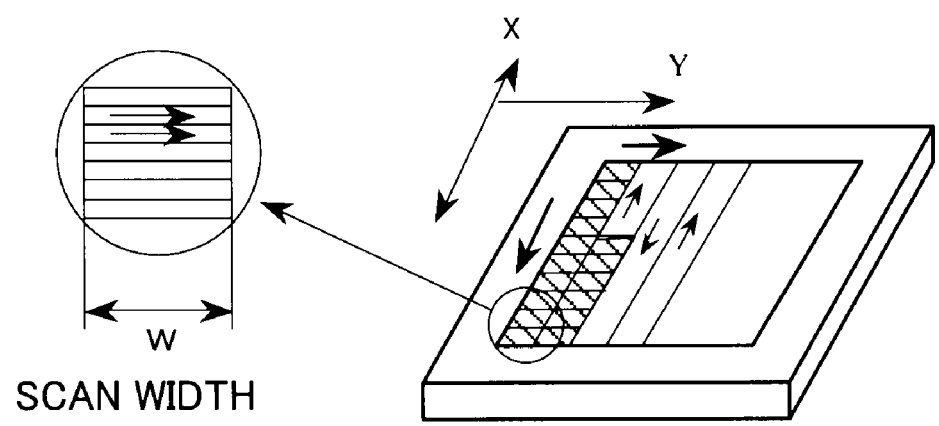
FIG. 3 is an explanatory view of inspection stripes of an inspected area in the first embodiment.

An inspected area in a pattern formed on a reticle 101, which is a measured sample, is virtually divided, as shown in FIG. 3, into inspection stripes in a strip shape having a scan width W. An inspection is performed by putting the reticle 101 on an XYθ table 102 shown in FIG. 2 and continuously moving a uniaxial stage so that the divided inspection stripes are continuously operated. When an inspection of one stripe is completed, another one axis is caused to make a step movement for observation of an adjacent stripe.

The reticle 101 is put on the XYθ table 102 using an autoloader 130 and an autoloader control circuit 113. However, a pattern may not always be in parallel with a running axis of the table. Thus, the reticle 101 is in most cases fixed onto a rotatable θ stage so that the reticle 101 can be mounted in parallel with the running axis. The aforementioned XYθ table 102 is controlled by using an X-axis motor, a Y-axis motor, a θ-axis motor, and a table control circuit 114. A moving distance of the XYθ table 102 is monitored by a laser length measuring system 122.

Moreover, the reticle defect inspection apparatus 100 includes an illuminating optical system 170 for irradiating the reticle 101 with an inspection light and a expanding optical system 104 for detecting a pattern image of the reticle 101 irradiated with an inspection light. A pattern formed on the reticle 101 is irradiated via the illuminating optical system 170 with a light emitted from a suitable light source 103 as an inspection light. The light inspection that passes through the reticle is incident on a photodiode array 105, which is an imaging means for inspection, via the expanding optical system 104. A portion of a strip-shaped area of the virtually divided pattern shown in FIG. 3 is expanded on the photodiode array 105 before being formed as an optical image (pattern image). The expanding optical system 104 is controlled by an autofocus control circuit 142 in order to maintain good image-forming conditions.

Photoelectric conversion of a pattern image formed on the photodiode array 105 is made by the photodiode array 105 and further A/D conversion by a sensor circuit 106. Measured image data output from the sensor circuit 106 is sent to a comparing circuit 108 together with data indicating the position of the reticle 101 on the XYθ table 102 output from a position circuit 107.

Design data used for pattern formation of the reticle 101, on the other hand, is read from a magnetic disk 109 to a deployment circuit 140 via a control computer 110. The read design data is converted by the deployment circuit 140 into two-valued or multi-valued design image data, which is sent to a reference circuit 144. The reference circuit 144 performs suitable filter processing on the sent graphic design image data.

The filter processing is performed because a filter has acted on measured pattern data acquired from the sensor circuit 106 due to resolution characteristics of the expanding optical system 104, an aperture effect of the photodiode array 105 or the like and thus, the filter processing is performed also on the design image data to adjust the design image data to the measured image data. The comparing circuit 108 compares the measured image data with the design image data on which suitable filter processing has been performed based on an appropriate algorithm and, if both pieces of data do not match, determines that the reticle is defective.

In a reticle inspection apparatus in the present embodiment for inspecting for defects or foreign matter present in a pattern formed on the surface of a reticle, which is an inspected sample, a reticle pattern image is formed using an optical system similar to that of a high-resolution microscope. A reticle pattern image is acquired as image information using, for example, a CCD camera like the aforementioned photodiode array or an imaging device such as a line sensor, and the image information is compared with a reference image acquired or formed separately to detect defects or foreign matter in the pattern.

Incidentally, detailed configurations of an optical system of transmitted illumination, an optical system of reflected illumination, and a detecting optical system to realize a simultaneous inspection of transmission and reflection are not shown in FIG. 2. For realization of a simultaneous inspection of transmission and reflection, it is necessary to provide an optical system of transmitted illumination, an optical system of reflected illumination, and a detecting optical system corresponding to these optical systems, and further two systems of the comparing circuit 108 or the like for defect detection.

FIG. 1 is a diagram showing principal parts of an optical system and a control system of a reticle defect inspection apparatus in the present embodiment. Of the overall configuration shown in FIG. 2, a portion corresponding to the light source 103, the position circuit 107, the reticle 101, the XYθ table 102, the expanding optical system 104, the photodiode array 105, and the sensor circuit 106 is shown.

First, the optical system in FIG. 1 includes the light source 103 emitting a light of the wavelength 193 nm using an ultraviolet laser, for example, an ArF laser. The optical system also includes a beam expander 12 for expanding a light emitted from the light source 103 and an optical integrator 14 for making the light a two-dimensional light source. More specifically, a fly eye lens or a diffuser panel can be used as the optical integrator 14.

Moreover, the optical system includes a collimator 18 for making a light that passes through the optical integrator 14 parallel rays. A first beam splitter 20 has a function of splitting parallel rays that have passed through the collimator 18 into a transmitted illumination light, which is a first inspection light, and a reflected illumination light, which is a second inspection light. Here, an optical system from the first beam splitter 20 up to irradiation of the reticle 101, which is an inspection sample on the table 102 with the transmitted illumination light, which is the first inspection light, is called an optical system of transmitted illumination. An optical system up to irradiation of the reticle 101, which is the inspection sample, with the reflected illumination light, which is the second inspection light, is called an optical system of reflected illumination.

The optical system of transmitted illumination and the optical system of reflected illumination are each configured so that the transmitted illumination light and the reflected illumination light are provided as Koehler illumination at positions of a transmission field stop 22 and a reflection field stop 24 respectively. In this specification, "a transmission field stop" means a field stop in the optical system of transmitted illumination and "a reflection field stop" means a field stop in the optical system of reflected illumination. The position of the transmission field stop 22 is set in such a way that the position and a pattern surface of the reticle 101 are conjugate and an area regulated and illuminated by the transmission field stop 22 becomes a transmitted illumination area. A first pulse motor 26 for driving the transmission field stop 22 is also provided to set a viewing position. Moreover, a condenser lens 30 is arranged so that a light, after passing through the transmission field stop 22, is provided as Koehler illumination on the pattern surface of the reticle 101.

The position of the reflection field stop 24, on the other hand, is set in such a way that the position and the pattern surface of the reticle 101 are conjugate and an area regulated and illuminated by the reflection field stop 24 becomes a reflected illumination area. A second pulse motor 34 for driving the reflection field stop 24 is also provided to set a viewing position. Moreover, a collimator 36 and an objective lens 38 are also arranged so that a light, after passing through the reflection field stop 24, is provided as Koehler illumination on the pattern surface of the reticle 101. A second beam splitter 40 is provided between the collimator 36 and the objective lens 38 to introduce a reflected illumination light onto the pattern surface.

In addition, the reticle defect inspection apparatus according to the embodiments of the present invention includes a detecting optical system that can simultaneously detect a transmitted light by irradiation of the reticle 101 with the first inspection light and a reflected light by irradiation of the sample with the second inspection light. First, the objective lens 38 for condensing both the transmitted light and reflected light is provided as a component of the detecting optical system. Further, a third beam splitter 42 for separating the light condensed by the objective lens 38 into a transmitted light and a reflected light is provided. Also, a first image-forming optical system 44 for forming an image of the transmitted light separated by the third beam splitter 42 and a second image-forming optical system 46 for forming an image of the reflected light separated by the third beam splitter 42 are provided.

Further, the reticle defect inspection apparatus according to the embodiments of the present invention includes a first imaging sensor 54, which is an imaging means for inspection of pattern images by the transmitted light whose image is formed by the first image-forming optical system 44, and a second imaging sensor 56, which is an imaging means for inspection of pattern images by the reflected light whose image is formed by the second image-forming optical system 46.

Further, the reticle defect inspection apparatus according to the embodiments of the present invention includes an imaging means for observation for checking a reticle (a so-called defect review) by causing the reticle to stop after moving the reticle to defective coordinates when a defect is detected in the defect inspection performed while the reticle is moved. The imaging means for observation is provided independently of the first imaging sensor 54 and the second imaging sensor 56, which are imaging means for inspection of pattern images obtained by the detecting optical system. This is because TDI sensors are normally used for the first imaging sensor 54 and the second imaging sensor 56 to efficiently inspect a moving reticle, but the TDI sensor is unsuitable for observation of a reticle at rest from a viewpoint of characteristics thereof.

The imaging means for observation includes a mirror 60 insertable by a pulse motor (not shown) or the like, a third image-forming optical system 62 that causes a pattern image of a defective portion to be formed from a light introduced by the mirror 60, and a third imaging sensor 58 such as a CCD to pick up an image formed by the third image-forming optical system 62 on an optical path between the objective lens 38 and the third beam splitter 42. In view of the role of observing an image of reticle at rest, the third imaging sensor is preferably a two-dimensional imaging sensor such as a CCD or CMOS sensor array. A pattern image acquired by the third imaging sensor 58 is observable after being displayed on a display device such as a pattern monitor 118.

Further, the reticle defect inspection apparatus according to the embodiments of the present invention includes a dose monitoring part for measuring a dose of laser light to the reticle 101 from the light source 103. More specifically, the dose monitoring part includes, for example, a beam splitter for dose monitoring 70 provided on an optical path of laser light emitted from the light source 103 and a dose sensor 72 such as an energy meter using, for example, a photodiode or black body radiation.

In addition, the reticle defect inspection apparatus includes a dose calculation/comparison circuit 74 that calculates accumulated irradiation with light shone on the same location of a reticle from the dose measured by the dose monitoring part and compares the accumulated irradiation with a preset threshold as a comparing part. The dose calculation/comparison circuit 74 always calculates accumulated irradiation by adding a dose input into the dose sensor 72 and stores the accumulated irradiation, for example, in a memory provided in the circuit. In addition, the dose calculation/comparison circuit 74 has a function to always compare the accumulated irradiation with the threshold of the accumulated irradiation, which is also input and stored in the memory in the circuit, to be performed by hardware such as circuit board or by software.

The reticle defect inspection apparatus in the present invention includes a light source control circuit 76 as a stop mechanism to stop irradiation of a reticle with laser light to avoid damage of the reticle when, as a result of comparison of the accumulated irradiation and the threshold, the dose calculation/comparison circuit 74 determines that the accumulated irradiation has exceeded the threshold. The light source control circuit 76 stops irradiation of a reticle with a laser light based on a decision made by the dose calculation/comparison circuit 74. More specifically, the stop mechanism of irradiation with the laser light may use any mechanism such as a mechanism to turn of the light source itself, a mechanism to block light by a shutter or the like, or a mechanism to bend an optical path itself by insertion of a mirror.

The threshold of the accumulated irradiation so as not to cause damage of a reticle is determined by considering various factors such as the wavelength and intensity of an irradiated inspection light, reticle material, and the degree of damage permissible as reticle specifications.

The reticle defect inspection apparatus according to the embodiments of the present invention, the accumulated irradiation of inspection light shone on the same location of a reticle can easily be controlled to below a level at which damage is caused. Thus, damage of a reticle caused by irradiation with an inspection light when inspecting the reticle while the reticle is caused to be at rest can be controlled.

Further, the reticle defect inspection apparatus preferably has a mechanism to restart irradiation of a reticle when a preset relaxation time elapses after irradiation of the reticle with a laser light is stopped. After some relaxation time elapses, damage may not be caused even if the same location of the reticle is irradiated with an inspection light. In such a case, there is an advantage that observation of the reticle is subsequently enabled again by the above mechanism after a predetermined relaxation time elapses.

More specifically, for example, a timer is provided in the dose calculation/comparison circuit 74 so that a mechanism to judge whether a relaxation time has elapsed can be created by monitoring an elapsed time after stopping irradiation and comparing the elapsed time with the relaxation time stored in a memory in the dose calculation/comparison circuit 74. The mechanism can be made to work so that, if the dose calculation/comparison circuit 74 determines that the relaxation time has elapsed, a control signal is sent to the light source control circuit 76 and irradiation of the reticle is restarted by the control signal from the light source control circuit 76. Or, the light source control circuit 76 itself may be made to have a mechanism to judge whether the relaxation time has elapsed.

Further, the reticle defect inspection apparatus preferably has an image storing part for storing a pattern image to be observed, a storage mechanism to cause the image storing part to store the pattern image immediately before stopping irradiation of the reticle with a laser light, and a display part for displaying the pattern image while irradiation of the reticle is stopped. With the configuration described above, observation of defective portions can be continued while the laser light is stopped, improving inspection efficiency.

More specifically, for example, an observation image storage device 78 such as a hard disk or semiconductor memory connected to the third imaging sensor 58 is provided as an image storing part. In addition, the pattern monitor 118, for example, a CRT is provided as a display part for displaying a pattern image and is connected to the observation image storage device 78. Further, by connecting the dose calculation/comparison circuit 74 and the observation image storage device 78, a mechanism to output a control signal for saving a pattern image immediately before stopping irradiation of the reticle with the laser light from the dose calculation/comparison circuit 74 to the observation image storage device 78 is realized. This makes it possible to cause the observation image storage device 78, which is an image storing part, to store a pattern image immediately before stopping irradiation of the reticle with the laser light. Further, by connecting the observation image storage device 78 and the pattern monitor 118, it becomes possible to display the stored pattern image on the pattern monitor 118, which is a display part, by the control signal from the dose calculation/comparison circuit 74.

Next, the reticle defect inspection method in the present embodiment will be described with reference to FIG. 1.

First, the reticle 101 is moved to inspect the reticle 101 for defects and when a defect is detected the XYθ table 102 is moved so that defective coordinates so that the a defect can be observed. Next, the reticle 101 is irradiated with a laser light, which is an inspection light, while the XYθ table 102 is caused to be at rest, the mirror 60 is inserted between the objective lens 38 and the third beam splitter 42, an image pattern of the defective portion is picked up by the third imaging sensor 58, and the image pattern is displayed on the pattern monitor 118 for observation (inspection).

Simultaneously with the start of observation, monitoring of a laser light dose to the reticle 101 is started by using the dose sensor 72. When the accumulated irradiation exceeds a preset threshold, for example, when the dose calculation/comparison circuit 74 determines that the threshold has been exceeded, irradiation of the reticle 101 with the laser light is stopped. The stop may automatically be caused or artificially be stopped after being confirmed that the accumulated irradiation has exceeded the threshold.

Further, it is preferable to restart irradiation of a reticle when a preset relaxation time elapses after irradiation of the reticle with a laser light is stopped. This is because observation of the reticle is thereby enabled again after a predetermined relaxation time elapses.

Further, for example, the observation image storage device 78 is caused to store a pattern image immediately before stopping irradiation of the reticle to prevent damage. In addition, it is preferable to display the pattern image stored in the observation image storage device 78, for example, on the pattern monitor 118 in an interval after stopping irradiation and before restarting it. This method enables observation in a time slot when observation of a defect detected portion is originally impossible, further improving inspection efficiency.

In the present embodiment, the dose is monitored by directly monitoring a laser light from a light source after being branched. However, dose monitoring is not limited to direct monitoring and, for example, the dose may indirectly be monitored by monitoring the passage of irradiation time before calculating the accumulated irradiation.

Second Embodiment

A reticle defect inspection apparatus according to the embodiment of the present invention is the same as that in the first embodiment except that the reticle to be a measured sample is a reflection type reticle for EUV exposure and the illuminating optical system consists exclusively of an optical system of reflected illumination and thus, a description thereof is omitted. Also, a reticle defect inspection method in the present embodiment is basically the same as that in the first embodiment except that a reticle for EUV exposure is used and thus, a description thereof is omitted.

Figure 4:
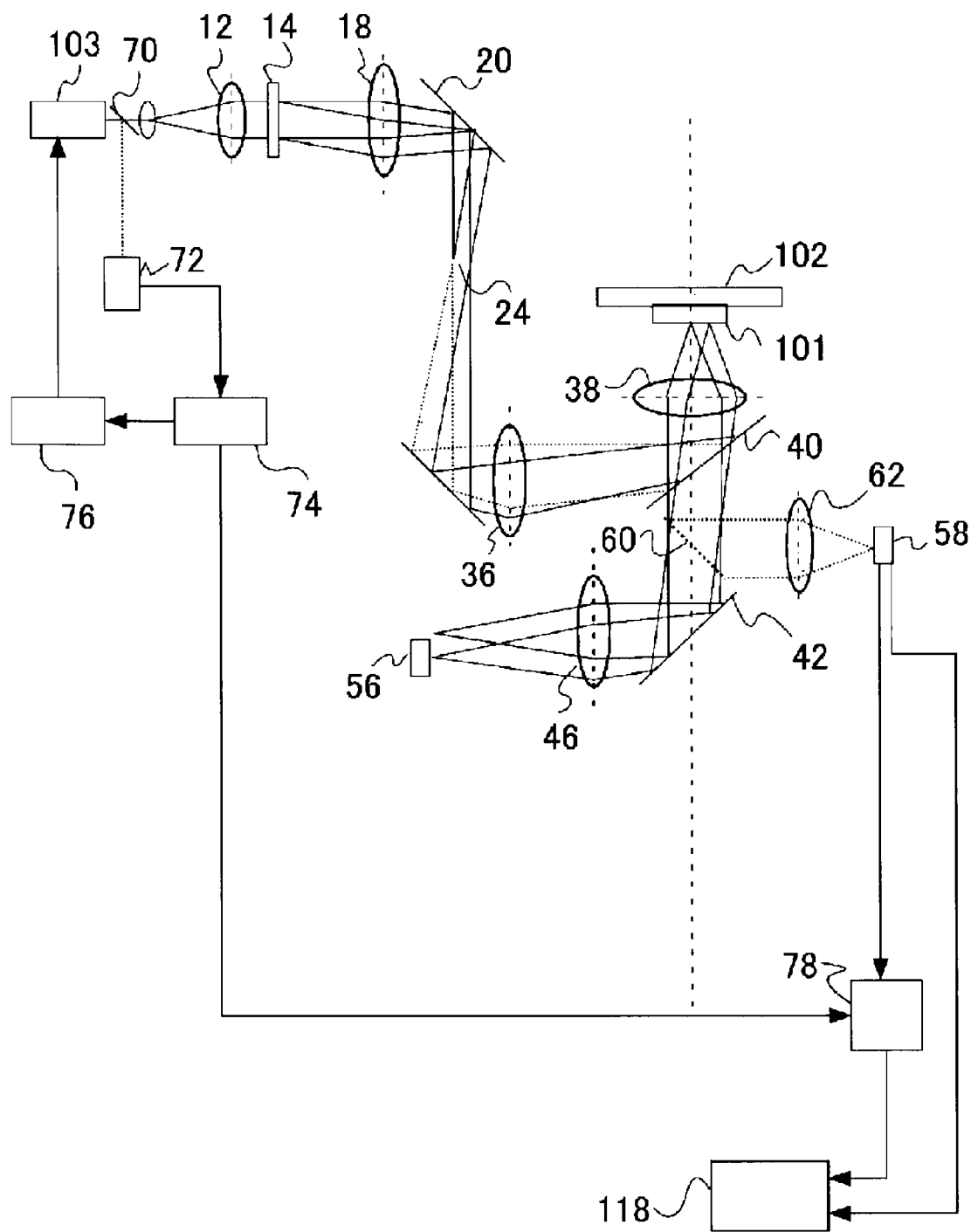
FIG. 4 is a diagram showing principal parts of an optical system and a control system of a reticle defect inspection apparatus in a second embodiment.

FIG. 4 is a diagram showing principal parts of an optical system and a control system of a reticle defect inspection apparatus in the present embodiment. As shown in FIG. 4, the reticle defect inspection apparatus in the present embodiment has no optical system of transmitted illumination and is configured to perform a reticle inspection exclusively by an optical system of reflected illumination. This is because the reticle, which is a sample to be inspected, is a reflection type reticle for EUV exposure and transmission observation is not practicable.

As described above, compared with a transmission reticle, such a reflection type reticle has no way out for inspection light and thus, energy due to irradiation with the inspection light tends to accumulate in a pattern portion. Therefore, it is conceivable that a problem of reticle damage will be serious. Consequently, like the present embodiment, the reticle defect inspection apparatus and reticle defect inspection method that can effectively control damage caused by irradiation with an inspection light when a reticle is at rest can be considered to be effective particularly for a reflection type reticle for EUV exposure.

Embodiments of the present invention have been described above with reference to concrete examples. Though a description of components that are not directly needed for describing the present invention such as a reticle defect inspection apparatus and a reticle defect inspection method is omitted when describing the embodiments, components needed for a reticle defect inspection apparatus or a reticle defect inspection method can suitably be selected and used.

In addition, all reticle defect inspection apparatuses and reticle defect inspection methods having components of the present invention and whose design can suitably be modified by a person skilled in the art are included in the scope of the present invention.

What is claimed is:

1. A reticle defect inspection apparatus for inspecting for defects on a reticle using a pattern image obtained by irradiating the reticle on which a pattern is formed with light, the apparatus comprising:
   a light source emitting the light;
   a dose monitoring part for measuring a dose of the light to the reticle surface;
   a calculating part for calculating a dose of the light accumulated on the reticle surface from the dose measured by the dose monitoring part;
   a comparing part for comparing the dose of the light accumulated on the reticle surface with a preset threshold; and
   a stop mechanism for stopping irradiation of the reticle with the light when, as a result of the comparison, the dose of the light accumulated on the reticle surface exceeds the threshold.

2. The apparatus according to claim 1, further comprising a mechanism to restart irradiation of the reticle with the light when a preset relaxation time elapses after irradiation of the reticle with the light is stopped.

3. The apparatus according to claim 1, further comprising:
   an image storing part for storing the pattern image;
   a storage mechanism for causing the image storing part to store the pattern image immediately before stopping irradiation of the reticle with the light; and
   a display part for displaying the pattern image while irradiation of the reticle is stopped.

4. The apparatus according to claim 1, wherein the reticle is a reflection type reticle for EUV exposure.

5. A reticle defect inspection method for inspecting for defects on a reticle using a pattern image obtained by irradiating the reticle on which a pattern is formed with light, the method comprising:
   inspecting the pattern image by irradiating the reticle surface with the light while the reticle is at rest; and
   stopping irradiation of the reticle surface with the light when a dose of the light accumulated on the reticle surface exceeds a preset threshold.

6. The method according to claim 5, further comprising restarting irradiation of the reticle with the light when a preset relaxation time elapses following a stop after irradiation of the reticle with the light is stopped.

7. The method according to claim 6, further comprising:
   storing the pattern image immediately before stopping irradiation of the reticle with the light; and
   displaying the stored pattern image after stopping irradiation of the reticle with the light and before restarting irradiation of the reticle with the light.

8. The method according to claim 5, wherein the reticle is a reflection type reticle for EUV exposure.

9. The apparatus according to claim 1, wherein the dose monitoring part includes a beam splitter provided on an optical path of the laser light emitted from the light source and a dose sensor configured to receive light split by the beam splitter.

10. The apparatus according to claim 1, wherein the dose monitoring part is located on an optical path between the light source and the reticle.

* * * * *